US008592407B2

(12) United States Patent
Ahmed et al.

(10) Patent No.: US 8,592,407 B2
(45) Date of Patent: Nov. 26, 2013

(54) **PYRROLO[2,1-*C*][1,4] BENZODIAZEPINE DERIVATIVES WITH DITHIOCARBAMATE SIDE CHAINS AND PROCESS FOR THE PREPARATION THEREOF**

(75) Inventors: Kamal Ahmed, Hyderabad (IN); Sreekanth Kokkonda, Andhra Pradesh (IN); Praveen K. Pogula, Andhra Pradesh (IN); Balakishan Gorre, Andhra Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 30 days.

(21) Appl. No.: 13/129,935

(22) PCT Filed: Mar. 24, 2009

(86) PCT No.: PCT/IN2009/000193
§ 371 (c)(1),
(2), (4) Date: Jan. 4, 2012

(87) PCT Pub. No.: WO2010/058414
PCT Pub. Date: May 27, 2010

(65) Prior Publication Data

US 2012/0101270 A1 Apr. 26, 2012

(30) Foreign Application Priority Data

Nov. 19, 2008 (IN) .......................... 2600/DEL/2008

(51) Int. Cl.
*C07D 487/04* (2006.01)
*A61K 31/5517* (2006.01)
*A61P 25/00* (2006.01)

(52) U.S. Cl.
USPC .......................................... 514/220; 540/496

(58) Field of Classification Search
USPC .......................................... 540/496; 514/220
See application file for complete search history.

(56) References Cited

FOREIGN PATENT DOCUMENTS

WO WO-2005063759 A1 7/2005
WO WO-2006003670 A1 1/2006

*Primary Examiner* — Bruck Kifle
(74) *Attorney, Agent, or Firm* — Edwards Wildman Palmer LLP; Barry Kramer; Nicholas J. DiCeglie, Jr.

(57) ABSTRACT

The present invention provides synthesis and in vitro anticancer activity of novel pyrrolo[2,1-c][1,4]benzodiazepine derivatives with dithiocarbamate side chains. The present invention also relates to a process for the preparation of new pyrrolo[2,1-c][1,4]benzodiazepine derivatives with dithiocarbamate side chains of general formula (A) and a process for the preparation thereof.

(A)

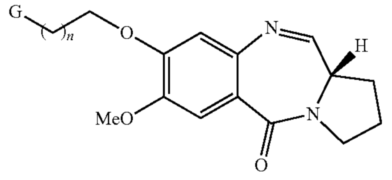

n = 1-9

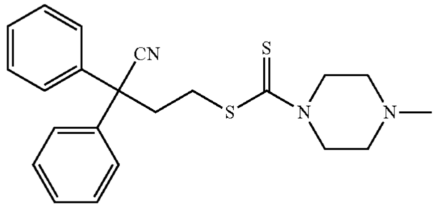

or

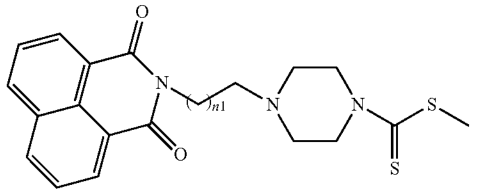

or

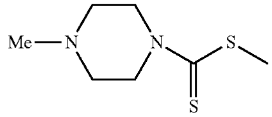

6 Claims, No Drawings

PYRROLO[2,1-*C*][1,4] BENZODIAZEPINE DERIVATIVES WITH DITHIOCARBAMATE SIDE CHAINS AND PROCESS FOR THE PREPARATION THEREOF

CROSS REFERENCE TO RELATED APPLICATIONS

This application is a U.S. National stage application pursuant to 35 U.S.C. §371 of International Application No. PCT/IN2009/000193, filed Mar. 24, 2009, which claims the benefit of priority of Indian Patent Application No. 2600/DEL/2008, filed Nov. 19, 2008, the disclosures of each of which are expressly incorporated herein by reference in their entireties.

FIELD OF THE INVENTION

The present invention relates to synthesis and in vitro anti-cancer activity of new pyrrolo[2,1-c][1,4]benzodiazepine derivatives with dithiocarbamate side chains. The present invention also relates to a process for the preparation of new pyrrolo[2,1-c][1,4]benzodiazepine derivatives with dithiocarbamate side chains of general formula A.

(Formula A)

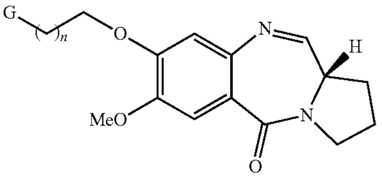

n = 1-9

-continued wherein G =

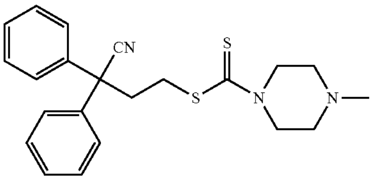

or

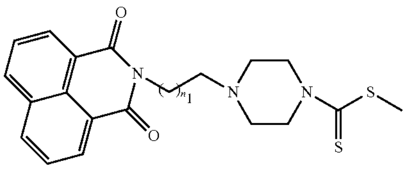

or

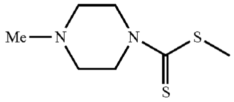

More particularly, the present invention relates to new pyrrolo[2,1-c][1,4]benzodiazepine derivatives with dithiocarbamate side chains of general formula A. The structural formulae of these pyrrolo[2,1-c][1,4]benzodiazepine derivatives with dithiocarbamate side chains is given below and is represented by the compounds of formula 12a-i, 13a-i and 14a-i.

12 a-i

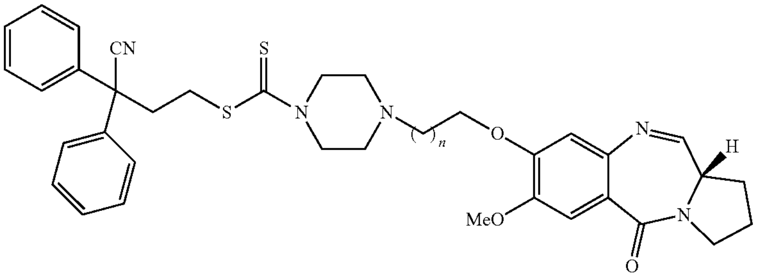

n = 1-9

13 a-i

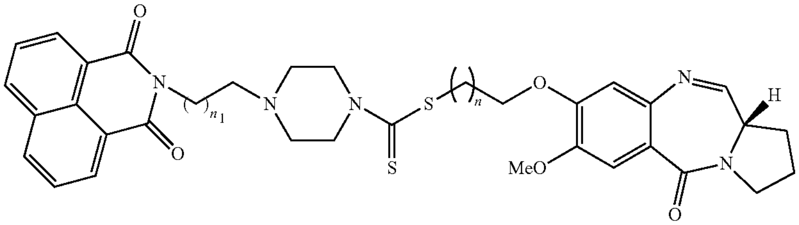

n = 1-9, $n_1$ = 2

-continued

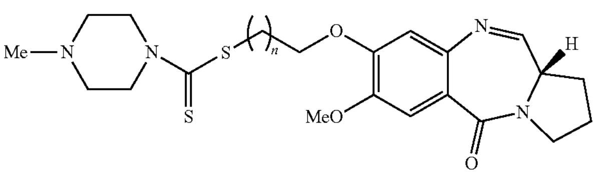

14 a-i n = 1-9

The present invention also relates to a process for the preparation of 3-cyano-3,3-diphenylpropyl4-(n-[(11aS)-7-(methyloxy)-5-oxo-2,3,5,11a-tetrahydro-1H-benzo[e]pyrrolo[1,2-a][1,4]diazepin-8-yl]oxyalkyl)hexahydro-1-pyrazinecarbodithioate/n-[(11aS)-7-(methyloxy)-5-oxo-2,3,5,11a-tetrahydro-1H-benzo[e]pyrrolo[1,2-a][1,4]diazepin-8-yl]oxyalkyl4-[3-(1,3-dioxo-2,3-dihydro-1H-benzo[de]isoquinolin-2-yl)propyl]hexahydro-1-pyrazinecarbodithioate/n-[(11aS)-7-(methyloxy)-5-oxo-2,3,5,11a-tetrahydro-1H-benzo[e]pyrrolo[1,2-a][1,4]diazepin-8-yl]oxyalkyl4-methyl hexahydro-1-pyrazinecarbodithioate with aliphatic chain length variation of these compounds and it also describes the DNA binding, anticancer (antitumour) activity.

BACKGROUND OF THE INVENTION

Naturally occurring pyrrolo[2,1-c][1,4]benzodiazepines belong to a group of antitumour antibiotics derived from *Streptomyces* species. Recently, there is much impetus for the PBD systems as they can recognize and bind to specific sequence of DNA. Examples of naturally occurring PBDs include anthramycin, DC-81, tomaymycin, sibiromycin and neothramycin.

Pyrrolo[2,1-c][1,4]benzodiazepine antitumour antibiotics are commonly known as anthramycin class of compounds. In the last few years, a growing interest has been shown in the development of new pyrrolo[2,1-c][1,4]benzodiazepine (PBDs). These antibiotics react covalently with DNA to form an N2-guanine adduct that lies within the minor groove of duplex DNA via an acid-labile aminal bond to the electrophilic imine at the N10-C11 position (Kunimoto, S.; Masuda, T.; Kanbayashi, N.; Hamada, M.; Naganawa, H.; Miyamoto, M.; Takeuchi, T.; and Unezawa, H. *J. Antibiot.,* 1980, 33, 665; Kohn, K. W. and Speous, C. L. *J. Mol. Biol.,* 1970, 51, 551; Hurley, L. H.; Gairpla, C. and Zmijewski, M. *Biochem. Biophys. Acta.* 1977, 475, 521; Kaplan, D. J. and Hurley, L. H. *Biochemistry,* 1981, 20, 7572). The molecules have a right-handed twist, which allows them to follow the curvature of the minor groove of B-form double-stranded DNA spanning three base pairs. Recently, PBD-naphthalimide hybrids have been synthesized that exhibit promising in vitro anticancer activity in certain cancer cell lines and have the potential to be developed as novel anti-cancer agents. (Kamal, A.; Srinivas, O.; Ramulu, P.; Ramesh, G.; KuMar, P. P. *Bioorg. Med. Chem. Lett.* 2003, 13, 3577; Kamal, A.; Reddy, B. S. N.; Reddy, G. S. K.; Ramesh, G.; *Bioorg. Med. Chem. Lea.* 2002, 12, 1933). A recent development has been the linking of alkylamines at C-8 position of PBD through alkane spacers, which exhibit cytotoxic activity in some cancer cell lines. Moreover, these compounds with improved lyphophilicity are promising for the development of new cytotoxic agents (Kamal, A.; Laxman, N.; Ramesh, G.; Srinivas, O.; Ramulu, P.; *Bioorg. Med. Chem. Lett.* 2002, 12, 1919). Some examples of such PBD hybrids are illustrated in FIG. 1.

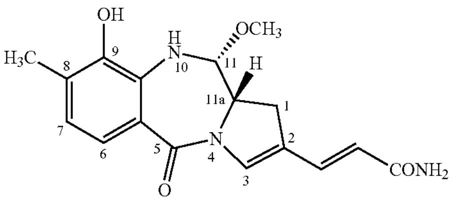

anthramycin

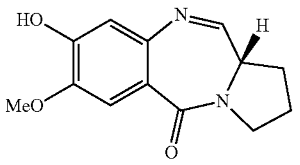

DC-81 a

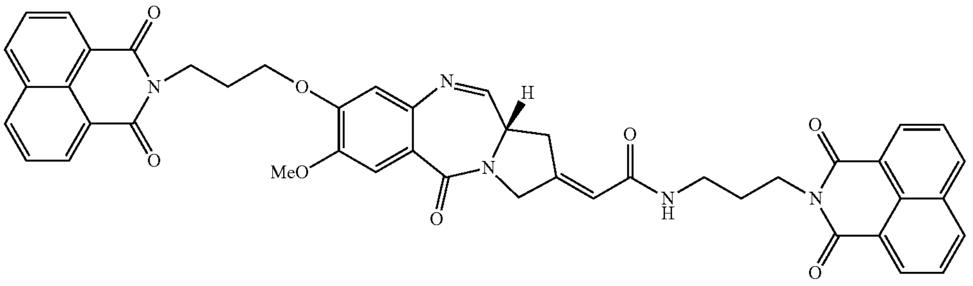

-continued b

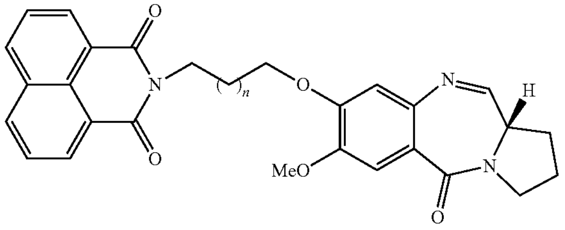

n = t-3, 6, 8
FIG. 1 c

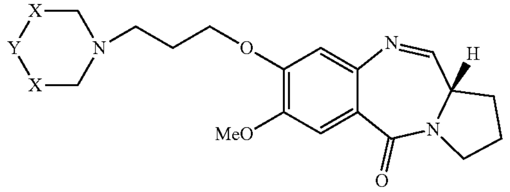

a; x = $CH_2$, Y = O
b; x = $CH_2$, Y = N—$Ch_3$

Dithiocarbamic acid esters are a common class of organic molecules. These simple molecules have shown remarkable antitumour properties, whose mode of action is thought to result from their derivatives in view of potent phase II enzyme inducers which could be used as cancer chemo preventive agents (Gerhauser, C.; You, M.; Pezzuto, J. M. *Cancer Res.* 1997, 57, 272; Li, R. T.; Cheng, T. M.; Cui, J. R. C. N. Patent 01118399.3, 2004. X.; Wang, R. Q.; Cui, J. R.; Li, R. T.; Cheng, T. M.; Ge, Z. M. *Chin. J. Clin. Pharmacol. Ther.* 2004, 9, 59).

A variety of 4-substituted-piperazine-1-carbodithioic acid 3-cyano-3,3-diphenyl-propyl esters have been synthesized and evaluated for their in vitro anticancer activity (Hou, X.; Ge, Z.; Wang, T.; Guo, W.; Cui, J.; Cheng, T.; Lai, C.; Li, R. *Bioorg. Med. Chem. Lett.* 2006, 16, 4214). Based on the potent anticancer activity of pyrrolo[2,1-c][1,4]benzodiazepines and dithiocarbamic acid esters the new PBD hybrids have been designed and synthesized by linking 3-cyano-3,3-diphenylpropylhexahydro-1-pyrazinecarbodithioate at C8-position of pyrrolo[2,1-c][1,4]benzodiazepine with varying alkane spacers, similarly 2-(3-hexahydro-1-pyrazinyl-propyl)-2,3-dihydro-1H-benzo[de]isoquinoline-1,3-dione and 1-methylhexahydropyrazine moieties linked at C8-position of pyrrolo[2,1-c][1,4]benzodiazepine with varying dithiocarbamate side chains.

OBJECTIVES OF THE INVENTION

The main objective of the present invention is to provide synthesis and in vitro anticancer activity of new pyrrolo[2,1-c][1,4]benzodiazepine derivatives with dithiocarbamate side chains.

Yet another object of the present invention is to provide a process for the preparation of new pyrrolo[2,1-c][1,4]benzodiazepine derivatives with dithiocarbamate side chains.

SUMMARY OF THE INVENTION

Accordingly the present invention provides a process for the preparation of a new pyrrolo[2,1-c][1,4]benzodiazepine derivatives with dithiocarbamate side chains of general formula A.

Formula A

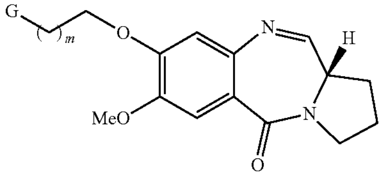

n = 1-9 wherein G =

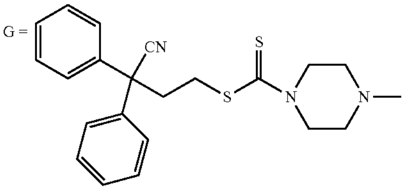

or

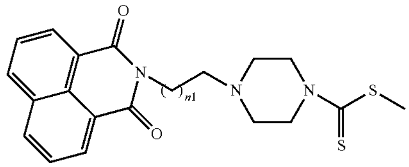

or

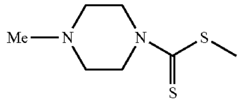

In an embodiment of the present invention the new pyrrolo[2,1-c][1,4]benzodiazepine derivatives with dithiocarbamate side chains of general formula A is represented by the formulae 12a-i, 13a-i and 14a-i.

Formula 12

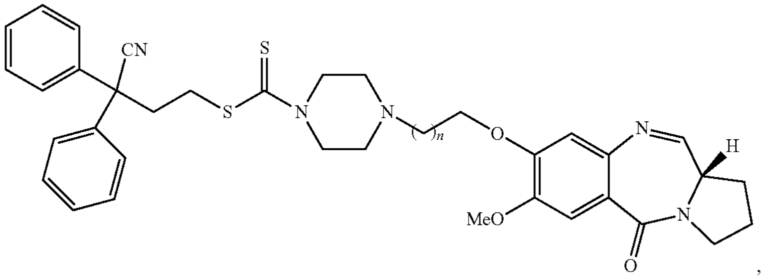

, where n = 1-9

-continued

Formula 13

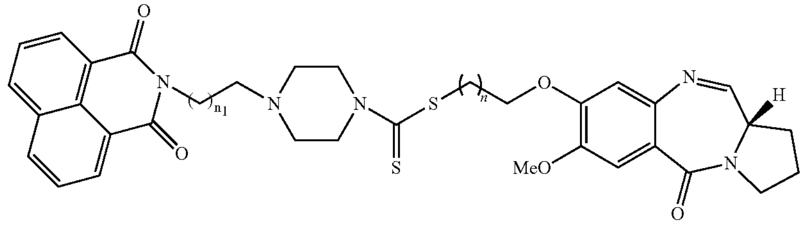

where n = 1-9, $n_1$ = 2

Formula 14

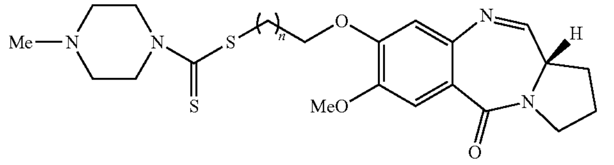

where n = 1-9

The present invention provides a process for preparation of a new pyrrolo[2,1-c][1,4]benzodiazepine derivatives with dithiocarbamate side chains of formula 12a-i, 13a-i and 14a-i which comprises of a) Reacting (2S)-2-[di(ethylsulfanyl)methyl]tetrahydro-1H-1-pyrrolyl[4-hydroxy-5-(methyloxy)-2-nitrophenyl]methanone of formula 1

1

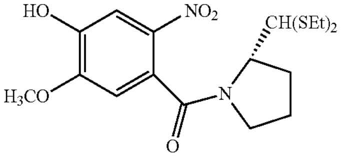

with dibromoalkanes in presence of acetone/$K_2CO_3$ at reflux temperature for a period of 48 h, isolating [4-[(n-bromoalkyl)oxy]-5-(methyloxy)-2-nitrophenyl](2S)-2-[di(ethylsulfanyl)methyl]tetrahydro-1H-1-pyrrolylmethanone 2a-i, 2 a-i

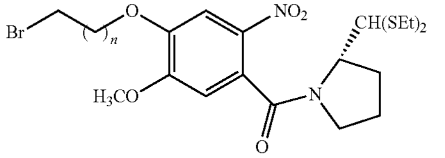

reacting these compounds with 3-cyano-3,3-diphenylpropylhexahydro-1-pyrazinecarbodithioate 3,2-(n-hexahydro-1-pyrazinylpropyl)-2,3-dihydro-1H-benzo[de]isoquinoline-1,3-dione 4, and 1-methylhexahydropyrazine of formula 5,

3

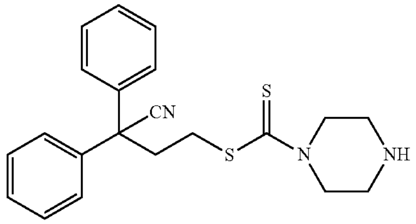

4

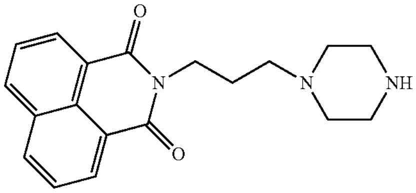

5

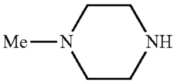

isolating 3-cyano-3,3-diphenylpropyl4-(n-[4-((2S)-2-[di(ethylsulfanyl)methyl]tetrahydro-1H-1-pyrrolylcarbon-yl)-2-(methyloxy)-5-nitrophenyl]oxyalkyl)hexahydro-1-pyrazinecarbodithioate of formula 6a-i, 6 a-i

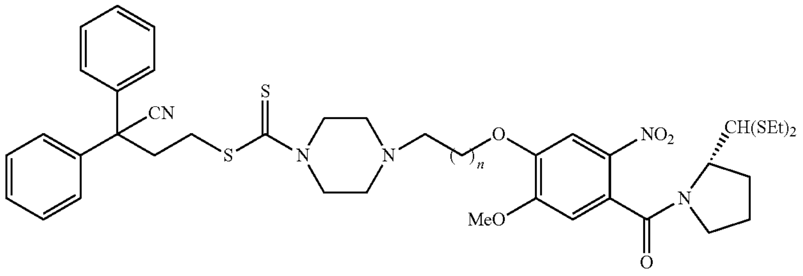

n = 1-9 n-[4-((2S)-2-[di(ethylsulfanyl)methyl]tetrahydro-1H-1-pyrrolylcarbonyl)-2-(methyloxy)-5-nitrophenyl]oxyalkyl4-[3-(1,3-dioxo-2,3-dihydro-1H-benzo[de]isoquinolin-2-yl)propyl]hexahydro-1-pyrazinecarbodithioate of formula 7a-i 7 a-i

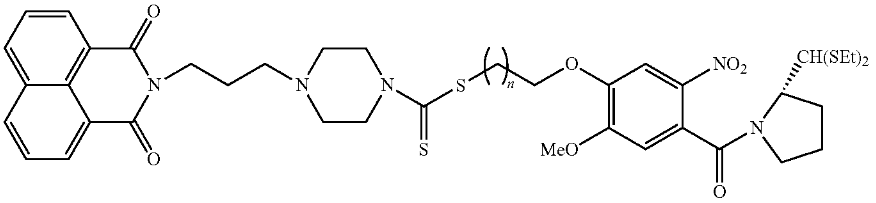

n = 1-9 and n-[4-((2S)-2-[di(ethylsulfanyl)methyl]tetrahydro-1H-1-pyrrolylcarbonyl)-2-(methyloxy)-5-nitrophenyl]oxyalkyl4-nethylhexahydro-1-pyrazinecarbodithioate of formula 8a-i respectively, 8 a-i

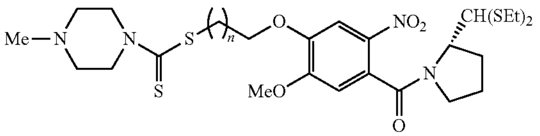

n = 1-9 b) Reducing the above nitro compounds of formula 6a-i, 7a-i and 8a-i with $SnCl_2.2H_2O$ in presence of organic solvent like methanol or ethanol up to a reflux temperature, isolating the 3-cyano-3,3-diphenylpropyl 4-(n-[5-amino-4-((2S)-2-[di(ethylsulfanyl)methyl]tetrahydro-1H-1-pyrrolylcarbonyl)-2-(methyloxy)phenyl]oxyalkyl)hexahydro-1-pyrazinecarbodithioate of formula 9a-i, 9 a-i

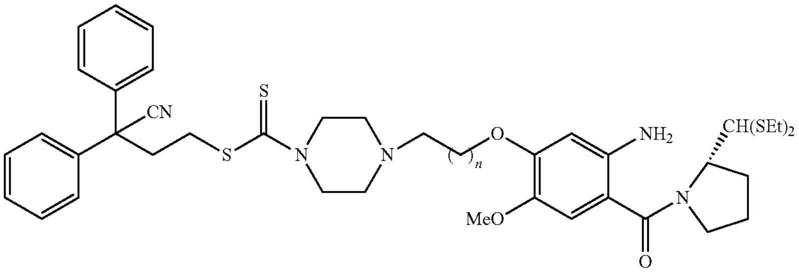

n = 1-9 n-[5-amino-4-((2S)-2-[di(ethylsulfanyl)methyl]tetrahydro-1H-1-pyrrolylcarbo-nyl)-2-(methyloxy)phenyl]oxyalkyl4-[3-(1,3-dioxo-2,3-dihydro-1H-benzo[de]isoquin-olin-2-yl)propyl]hexahydro-1-pyrazinecarbodithioate of formula 10a-i, 10 a-i

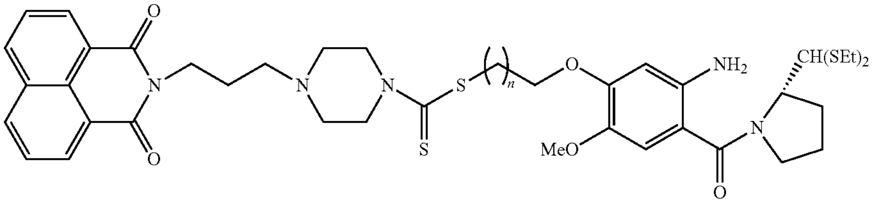

n = 1-9 and n-[5-amino-4-((2S)-2-[di(ethylsulfanyl)methyl]tetrahydro-1H-1-pyrrolyl carbonyl)-2-(methyloxy)phenyl]oxyalkyl4-methylhexahydro-1-pyrazinecarbo-dithioate of formula 11a-i respectively, 11 a-i

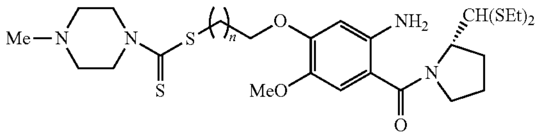

n = 1-9 c) Reacting the above said amino compounds of formula 9a-i, 10a-i and 11a-i obtained in step (b) with known deprotecting agents in a conventional manner to give novel pyrrolo[2,1-c][1,4]benzodiazepine hybrids of formula 12a-i, 13a-i and 14a-i.

12 a-i

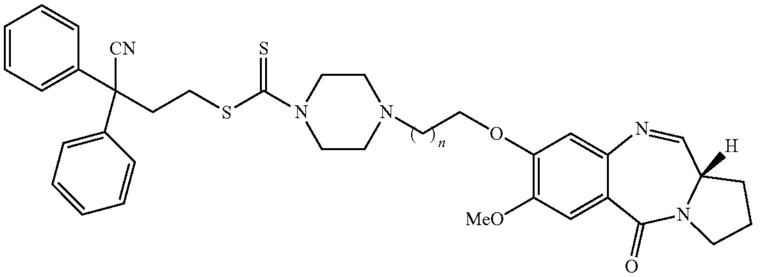

n = 1-9

13 a-i

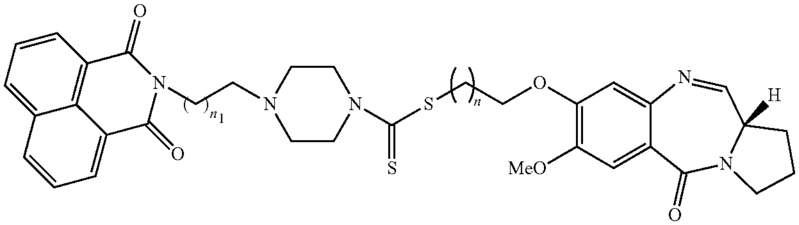

n = 1-9, $n_1$ = 2

14 a-i

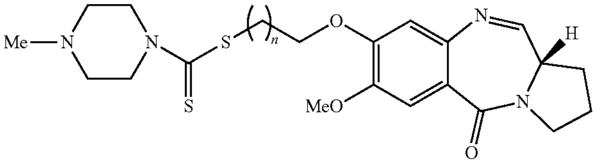

n = 1-9

DETAILED DESCRIPTION OF THE INVENTION

The precursors 3-cyano-3,3-diphenylpropylhexahydro-1-pyrazinecarbo-dithioate of formula 3 (Hou, X.; Ge, Z.; Wang, T.; Guo, W.; Cui, J.; Cheng, T.; Lai, C.; Li, R. *Bioorg. Med. Chem. Lett.* 2006, 16, 4214) and (2S)—N-[4-(hydroxy-5-methoxy-2-nitrobenzoyl]pyrrolidine-2-carboxaldehydediethylthio-acetal of formula 2 (Thurston, D. E.; Murthy, V. S.; Langley, D. R.; Jones, G. B. *Synthesis.* 19%, 81) have been prepared by literature methods.

Some representative compounds of formula 12, 13 and 14 for the present inventions are given below a) 3-cyano-3,3-diphenylpropyl 4-(3-[(11aS)-7-(methyloxy)-5-oxo-2,3,5,11a-tetrahydro-1H-benzo[e]pyrrolo[1,2-a][1,4]diazepin-8-yl]oxypropyl)hexahydro-1-pyrazinecarbodithioate (12b);

b) 3-cyano-3,3-diphenylpropyl 4-(4-[(11aS)-7-(methyloxy)-5-oxo-2,3,5,11a-tetrahydro-1H-benzo[e]pyrrolo[1,2-a][1,4]diazepin-8-yl]oxybutyl)hexahydro-1-pyrazinecarbodithioate (12c);

c) 3-cyano-3,3-diphenylpropyl 4-(5-[(11aS)-7-(methyloxy)-5-oxo-2,3,5,11a-tetrahydro-1H-benzo[e]pyrrolo[1,2-a][1,4]diazepin-8-yl]oxypentyl)hexahydro-1-pyrazinecarbodithioate (12d);

d) 3-[(11aS)-7-(methyloxy)-5-oxo-2,3,5,11a-tetrahydro-1H-benzo[e]pyrrolo[1,2-a][1,4]diazepin-8-yl]oxypropyl4-[3-(1,3-dioxo-2,3-dihydro-1H-benzo[de]isoquinolin-2-yl)propyl]hexahydro-1-pyrazinecarbodithioate (13b);

e) 4-[(11aS)-7-(methyloxy)-5-oxo-2,3,5,11a-tetrahydro-1H-benzo[e]pyrrolo[1,2-a][1,4]diazepin-8-yl]oxybutyl4-[3-(1,3-dioxo-2,3-dihydro-1H-benzo[de]isoquinolin-2-yl)propyl]hexahydro-1-pyrazinecarbodithioate (13c);

f) 5-[(11aS)-7-(methyloxy)-5-oxo-2,3,5,11a-tetrahydro-1H-benzo[e]pyrrolo[1,2-a][1,4]diazepin-8-yl]oxypentyl4-[3-(1,3-dioxo-2,3-dihydro-1H-benzo[de]isoquinolin-2-yl)propyl]hexahydro-1-pyrazinecarbodithioate (13d);

g) 4-[(11aS)-7-(methyloxy)-5-oxo-2,3,5,11a-tetrahydro-1H-benzo[e]pyrrolo[1,2-a][1,4]diazepin-8-yl]oxybutyl4-methylhexahydro-1-pyrazinecarbodithioate (14c);

h) 5-[(11aS)-7-(methyloxy)-5-oxo-2,3,5,11a-tetrahydro-1H-benzo[e]pyrrolo[1,2-a][1,4]diazepin-8-yl]oxypentyl4-methylhexahydro-1-pyrazinecarbodithioate (14d);

These new analogues of pyrrolo[2,1-c][1,4]benzodiazepine hybrids linked at C-8 position have shown promising DNA binding activity and efficient anticancer activity in various cell lines. The molecules synthesized are of immense biological significance with potential sequence selective DNA-binding property. This present invention is illustrated in Scheme 1, Scheme 2 and Scheme 3 which comprise:

1) The ether linkage at C-8 position of DC-81 intermediates with dithiocarbamate side chains.

2) Synthesis of C-8 linked PBD antitumour antibiotic hybrid imines.

3) Purification by column chromatography using different solvents like ethyl acetate, hexane, chloroform and methanol.

Scheme 1
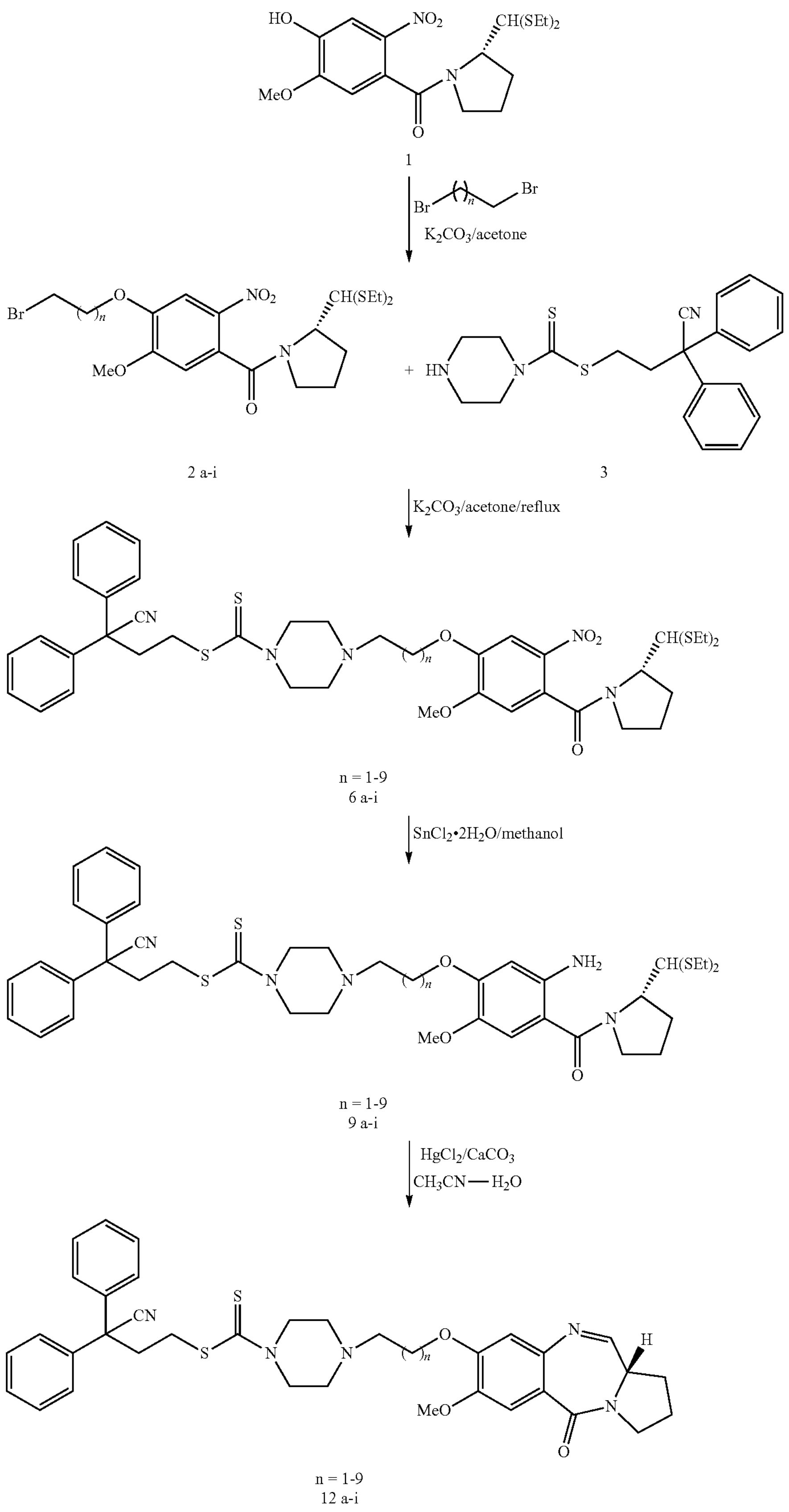

Scheme 2
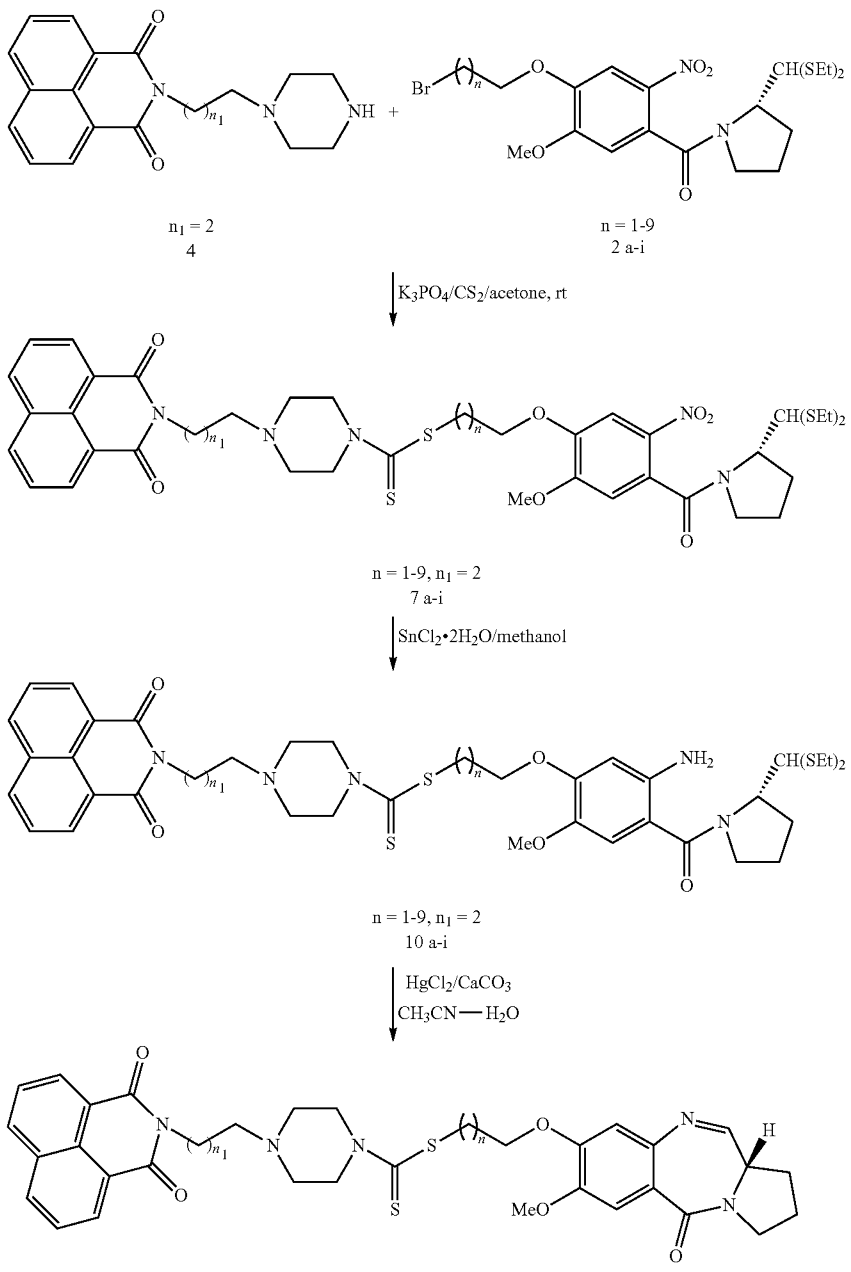
$n_1 = 2$
4
n = 1-9
2 a-i
n = 1-9, $n_1 = 2$
7 a-i
n = 1-9, $n_1 = 2$
10 a-i
n = 1-9, $n_1 = 2$
13 a-i
Scheme 3
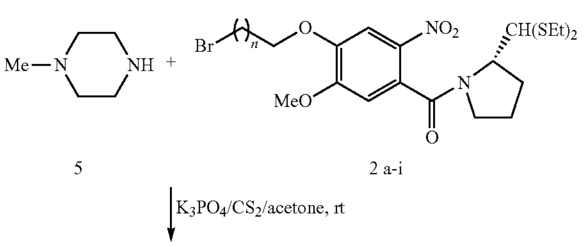
5
2 a-i
-continued
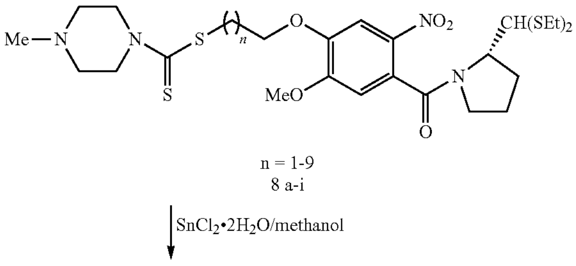
n = 1-9
8 a-i -continued

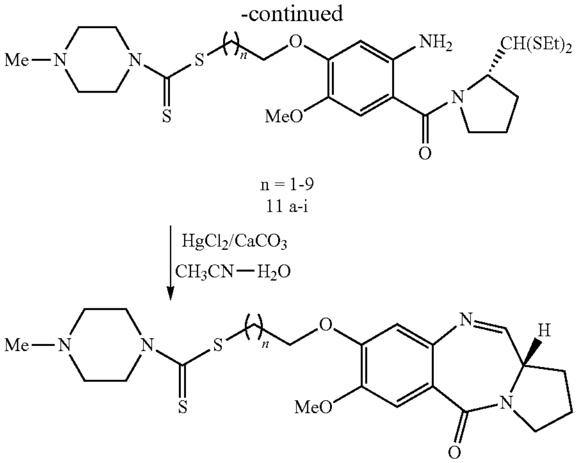

n = 1-9
11 a-i n = 1-9
14 a-i

The following examples are given by way of illustration of the working of the invention in actual practice and therefore should not be construed to limit the scope of present invention in any way.

Example 1

To a solution of [4-[(3-bromopropyl)oxy]-5-(methyloxy)-2-nitrophenyl](2S)-2-[di(ethylsulfanyl)methyl]tetrahydro-1H-1-pyrrolylmethanone 2a (521 mg, 1 mmol) in dry DMF (10 mL) was added anhydrous $K_2CO_3$ (552 mg, 4 mmol) and the 3-cyano-3,3-diphenylpropylhexahydro-1-pyrazinecarbodithioate 3 (381 mg, 1 mmol). The reaction mixture was stirred at room temperature for 48 h. TLC using ethyl acetate as a solvent system monitored the reaction. The potassium carbonate was removed by suction filtration and the solvent was removed under vacuum. The crude product thus obtained was purified by column chromatography using ethylacetate-hexane (1:1) as eluant to afford pure compound of 6a (657 mg, 80%). ESIMS: m/z 822 ($M^+$).

$^1$H NMR ($CDCl_3$): δ 7.71 (s, 1H), 7.56-7.24 (m, 10H), 6.83 (s, 1H), 4.88 (d, J=3.399, 1H), 4.76-4.67 (m, 1H), 4.31 (t, J=6.798, 2H), 4.18 (t, J=6.043, 2H), 3.95 (s, 3H), 3.83-3.52 (m, 1H), 3.43-3.33 (m, 2H), 3.32-3.17 (m, 2H), 2.88-2.65 (m, 4H), 2.63-2.49 (m, 4H), 2.37-2.21 (m, 1H), 2.18-2.02 (m, 2H), 1.86-1.61 (m, 4H), 1.40-1.29 (m, 6H), 1.28-1.22 (m, 2H), 1.02-0.81 (m, 2H).

The compound 6a (822 mg, 1 mmol) dissolved in methanol (20 mL) and added $SnCl_2.2H_2O$ (1.125 g, 5 mmol) was refluxed for 5 h or until the TLC indicated that reaction was completed. The methanol was evaporated by vacuum and the aqueous layer was then carefully adjusted to pH 8 with 10% $NaHCO_3$ solution and then extracted with ethyl acetate and chloroform (2×30 ml and 2×30 mL). The combined organic phase was dried over $Na_2SO_4$ and evaporated under vacuum to afford the crude amino diethyl thioacetal 9a (617 mg, 78%), which was used directly in the next step.

A solution of 9a (792 mg, 1 mmol), $HgCl_2$ (613 mg, 2.26 mmol) and $CaCO_3$ (246 mg, 2.46 mmol) in acetonitrile-water (4:1) was stirred slowly at room temperature for overnight or until TLC indicates complete loss of starting material. The reaction mixture was diluted with ethyl acetate (30 ml) filtered through a celite pad. The clear organic supernatant was extracted with saturated 5% $NaHCO_3$ (20 ml), brine (20 ml) and the combined organic phase is dried ($Na_2SO_4$). The organic layer was evaporated in vacuum and purified by column chromatography (95% $CH_2Cl_2$-MeOH) to give compound 12a (366 mg, 55%). This material was repeatedly evaporated from $CHCl_3$ in vacuum to generate the imine form.

Example 2

To a solution of [4-[(4-bromobutyl)oxy]-5-(methyloxy)-2-nitrophenyl](2S)-2-[di(ethylsulfanyl)methyl]tetrahydro-1H-1-pyrrolylmethanone 2b (535 mg, 1 mmol) in dry DMF (10 mL) was added anhydrous $K_2CO_3$ (552 mg, 4 mmol) and the 3-cyano-3,3-diphenylpropylhexahydro-1-pyrazinecarbodithioate 3 (381 mg, 1 mmol). The reaction mixture was stirred at room temperature for 48 h. TLC using ethyl acetate as a solvent system monitored the reaction. The potassium carbonate was removed by suction filtration and the solvent was removed under vacuum. The crude product thus obtained was purified by column chromatography using ethylacetate-hexane (1:1) as eluant to afford pure compound of 6b (668 mg, 80%). ESIMS: m/z 836 ($M^+$)

$^1$H NMR ($CDCl_3$): δ 7.67 (s, 1H), 7.50-7.25 (m, 10H), 6.83 (s, 1H), 4.88 (d, J=3.777, 1H), 4.76-4.61 (m, 1H), 4.31 (t, J=6.798, 2H), 4.13 (t, J=6.798, 2H), 3.95 (s, 3H), 3.79-3.71 (m, 1H), 3.68-3.61 (t, 1H), 3.52-3.45 (t, 1H), 3.43-3.33 (m, 2H), 3.32-3.17 (m, 2H), 2.88-2.65 (m, 4H), 2.63-2.42 (m, 4H), 2.37-2.21 (m, 2H), 2.19-2.04 (m, 2H), 2.03-1.88 (m, 2H), 1.86-1.53 (m, 4H), 1.40-1.22 (m, 6H), 1.03-0.82 (m, 2H).

The compound 6b (836 mg, 1 mmol) dissolved in methanol (20 mL) and added $SnCl_2.2H_2O$ (1.125 g, 5 mmol) was refluxed for 5 h or until the TLC indicated that reaction was completed. The methanol was evaporated by vacuum and the aqueous layer was then carefully adjusted to pH 8 with 10% $NaHCO_3$ solution and then extracted with ethyl acetate and chloroform (2×30 ml and 2×30 mL). The combined organic phase was dried over $Na_2SO_4$ and evaporated under vacuum to afford the crude amino diethyl thioacetal 9b (628 mg, 78%), which was used directly in the next step.

A solution of 9b (806 mg, 1 mmol), $HgCl_2$ (613 mg, 2.26 mmol) and $CaCO_3$ (246 mg, 2.46 mmol) in acetonitrile-water (4:1) was stirred slowly at room temperature for overnight or until TLC indicates complete loss of starting material. The reaction mixture was diluted with ethyl acetate (30 ml) filtered through a celite pad. The clear organic supernatant was extracted with saturated 5% $NaHCO_3$ (20 ml), brine (20 ml) and the combined organic phase is dried ($Na_2SO_4$). The organic layer was evaporated in vacuum and purified by column chromatography (95% $CH_2Cl_2$-MeOH) to give compound 12b (375 mg, 55%). This material was repeatedly evaporated from $CHCl_3$ in vacuum to generate the imine form. ESIMS: m/z 682 ($M^+$)

$^1$H NMR ($CDCl_3$): δ 7.67 (d, J=4.716, 1H), 7.55-7.24 (m, 10H), 6.82 (s, 1H), 6.34 (s, 1H), 4.02 (t, J=6.288, 2H), 3.93 (s; 3H), 3.80-3.61 (m, 1H), 3.45-3.31 (m, 2H), 2.90-2.75 (m, 2H), 2.61-2.37 (m, 4H), 2.36-2.24 (m, 2H), 2.13-1.98 (m, 2H), 1.96-1.83 (m, 2H), 1.80-1.62 (m, 4H), 1.36-1.10 (m, 4H), 1.02-0.80 (m, 2H).

Example 3

To a solution of [4-[(5-bromopentyl)oxy]-5-(methyloxy)-2-nitrophenyl](2S)-2-[di(ethylsulfanyl)methyl]tetrahydro-1H-1-pyrrolylmethanone 2c (549 mg, 1 mmol) in dry DMF (10 mL) was added anhydrous $K_2CO_3$ (552 mg, 4 mmol) and the 3-cyano-3,3-diphenylpropylhexahydro-1-pyrazinecarbodithioate 3 (381 mg, 1 mmol). The reaction mixture was stirred at room temperature for 48 h. TLC using ethyl acetate as a solvent system monitored the reaction. The potassium carbonate was removed by suction filtration and the solvent was removed under vacuum. The crude product thus obtained was purified by column chromatography using ethylacetate-hexane (1:1) as eluant to afford pure compound of be (680 mg, 80%). ESIMS: m/z 850 ($M^+$)

$^1$H NMR ($CDCl_3$): δ 7.66 (s, 1H), 7.50-7.23 (m, 10H), 6.82 (s, 1H), 4.88 (d, J=3.777, 1H), 4.77-4.67 (m, 1H), 4.31 (t, J=6.798, 2H), 4.09 (t, J=5.854, 2H), 3.94 (s, 3H), 3.83-3.52 (m, 1H), 3.44-3.33 (m, 2H), 3.32-3.17 (m, 2H), 2.90-2.65 (m, 4H), 2.62-2.48 (m, 4H), 2.47-2.38 (m, 2H), 2.37-2.22 (m, 2H), 2.19-2.00 (m, 1H), 1.98-1.86 (m, 2H), 1.77-1.48 (m, 4H), 1.41-1.29 (m, 6H), 1.28-1.21 (m, 2H), 1.03-0.83 (m, 2H).

The compound 6c (850 mg, 1 mmol) dissolved in methanol (20 mL) and added $SnCl_2.2H_2O$ (1.125 g, 5 mmol) was refluxed for 5 h or until the TLC indicated that reaction was completed. The methanol was evaporated by vacuum and the aqueous layer was then carefully adjusted to pH 8 with 10% $NaHCO_3$ solution and then extracted with ethyl acetate and chloroform (2×30 ml and 2×30 mL). The combined organic phase was dried over $Na_2SO_4$ and evaporated under vacuum to afford the crude amino diethyl thioacetal 9c (639 mg, 78%), which was used directly in the next step.

A solution of 9c (820 mg, 1 mmol), $HgCl_2$ (613 mg, 2.26 mmol) and $CaCO_3$ (246 mg, 2.46 mmol) in acetonitrile-water (4:1) was stirred slowly at room temperature for overnight. The reaction mixture was diluted with ethyl acetate (30 mL) filtered through a celite pad. The clear organic supernatant was extracted with saturated 5% $NaHCO_3$ (20 mL), brine (20 mL) and the combined organic phase was dried ($Na_2SO_4$). The organic layer was evaporated under vacuum and purified by column chromatography (95% $CH_2Cl_2$-MeOH) to give compound 12c (382 mg, 55%). This material was repeatedly evaporated from $CHCl_3$ in vacuum to generate the imine form.

Example 4

To a solution of 2-(3-hexahydro-1-pyrazinylpropyl)-2,3-dihydro-1H-benzo[de]isoquinoline-1,3-dione 4 (323 mg, 1 mmol) in dry acetone (10 mL) was added carbon disulfide 10 drops (~2.5 mmol) and anhydrous $K_3PO_4$ (425 mg, 2 mmol). The mixture was stirred <10° C. for 1 h. Than the [4-[(3-bromopropyl)oxy]-5-(methyloxy)-2-nitrophenyl](2S)-2-[di(ethylsulfanyl)methyl]tetrahydro-1H-1-pyrrolylmethanone 2a (521 mg, 1 mmol) The reaction mixture was stirred at room temperature for 12 h. TLC using ethylacetate as a solvent system monitored the reaction. The potassium phosphate was removed by suction filtration and the solvent was removed under vacuum. The crude product was purified by column chromatography using petroleum ether-ethylacetate (1:1) as eluent to afford pure compound of 7a (630 mg, 75%).

$^1$H NMR ($CDCl_3$): δ 8.58 (d, J=6.798, 2H), 8.21 (d, J=7.554 Hz, 2H), 7.83-7.71 (t, 2H), 7.68 (s, 1H), 6.81 (s, 1H), 4.87 (d, J=3.777 Hz, 1H), 4.74-4.66 (m, 1H), 4.35-4.15 (m, 6H), 3.95 (s, 3H), 3.50 (t, 2H), 3.34 (t, 2H), 3.30-3.20 (m, 1H), 2.87-2.67 (m, 4H), 2.60-2.49 (m, 5H), 2.42 (t, J=4.532, 2H), 2.37-2.21 (m, 2H), 2.19-2.03 (m, 1H), 2.02-1.89 (m, 3H), 1.87-1.72 (m, 1H) 1.47-1.22 (m, 6H), 1.00-0.83 (m, 1H).

The compound 7a (840 mg, 1 mmol) dissolved in methanol (20 mL) and added $SnCl_2.2H_2O$ (1.125 g, 5 mmol) was refluxed for 5 h or until the TLC indicated that reaction was completed. The methanol was evaporated by vacuum and the aqueous layer was then carefully adjusted to pH 8 with 10% $NaHCO_3$ solution and then extracted with ethyl acetate and chloroform (2×30 ml and 2×30 mL). The combined organic phase was dried over $Na_2SO_4$ and evaporated under vacuum to afford the crude amino diethyl thioacetal 10a (631 mg, 78%), which was used directly in the next step.

A solution of 10a (810 mg, 1 mmol), $HgCl_2$ (613 mg, 2.26 mmol) and $CaCO_3$ (246 mg, 2.46 mmol) in acetonitrile-water (4:1) was stirred slowly at room temperature for overnight. The reaction mixture was diluted with ethyl acetate (30 mL) filtered through a celite pad. The clear organic supernatant was extracted with saturated 5% $NaHCO_3$ (20 mL), brine (20 mL) and the combined organic phase was dried ($Na_2SO_4$). The organic layer was evaporated under vacuum and purified by column chromatography (95% $CH_2Cl_2$-MeOH) to give compound 13a (376 mg, 55%). This material was repeatedly evaporated from $CHCl_3$ in vacuum to generate the imine form.

$^1$H NMR ($CDCl_3$): δ 8.61 (d, J=7.346 Hz, 2H), 8.23 (d, J=8.081 Hz, 2H), 7.77 (t, J=8.081 Hz, J=7.346 Hz, 2H), 7.67 (d, J=5.143, 1H), 7.51 (s, 1H), 6.81 (s, 1H), 4.35-4.03 (m, 4H), 3.93 (s, 3H), 3.89-3.67 (m, 2H), 3.66-3.41 (m, 3H), 2.63-2.45 (m, 4H), 2.39-2.19 (m, 4H), 2.16-1.87 (m, 4H), 1.74-1.56 (m, 3H), 1.34-1.15 (m, 1H), 0.97-0.79 (m, 2H).

Example 5

To a solution of 2-(3-hexahydro-1-pyrazinylpropyl)-2,3-dihydro-1H-benzo[de]isoquinoline-1,3-dione 4 (323 mg, 1 mmol) in dry acetone (10 mL) was added carbon disulfide 10 drops (~2.5 mmol) and anhydrous $K_3PO_4$ (425 mg, 2 mmol). The mixture was stirred <10° C. for 1 h. Than the [4-[(4-bromobutyl)oxy]-5-(methyloxy)-2-nitrophenyl](2S)-2-[di(ethylsulfanyl)methyl]-tetrahydro-1H-1-pyrrolylmethanone 2b (535 mg, 1 mmol). The reaction mixture was stirred at room temperature for 12 h. TLC using ethylacetate as a solvent system monitored the reaction. The potassium phosphate was removed by suction filtration and the solvent was removed under vacuum. The crude product was purified by column chromatography using petroleum ether-ethylacetate (1:1) as eluent to afford pure compound of 7b (640 mg, 75%). ESIMS: m/z 854 ($M^+$)

The compound 7b (854 mg, 1 mmol) dissolved in methanol (20 mL) and added $SnCl_2.2H_2O$ (1.125 g, 5 mmol) was refluxed for 5 h or until the TLC indicated that reaction was completed. The methanol was evaporated by vacuum and the aqueous layer was then carefully adjusted to pH 8 with 10% $NaHCO_3$ solution and then extracted with ethyl acetate and chloroform (2×30 ml and 2×30 mL). The combined organic phase was dried over $Na_2SO_4$ and evaporated under vacuum to afford the crude amino diethyl thioacetal 10b (642 mg, 78%), which was used directly in the next step.

A solution of 10b (824 mg, 1 mmol), $HgCl_2$ (613 mg, 2.26 mmol) and $CaCO_3$ (246 mg, 2.46 mmol) in acetonitrile-water (4:1) was stirred slowly at room temperature for overnight or until TLC indicates complete loss of starting material. The reaction mixture was diluted with ethyl acetate (30 ml) filtered through a celite. The clear organic supernatant was extracted with saturated 5% $NaHCO_3$ (20 ml), brine (20 ml) and the combined organic phase is dried ($Na_2SO_4$). The organic layer was evaporated in vacuum and purified by column chromatography (95% $CH_2Cl_2$-MeOH) to give compound 13b (384 mg, 55%). This material was repeatedly evaporated from $CHCl_3$ in vacuum to generate the imine form.

Example 6

To a solution of 2-(3-hexahydro-1-pyrazinylpropyl)-2,3-dihydro-1H-benzo[de]isoquinoline-1,3-dione 4 (323 mg, 1 mmol) in dry acetone (10 mL) was added carbon disulfide 10 drops (~2.5 mmol) and anhydrous $K_3PO_4$ (425 mg, 2 mmol). The mixture was stirred <10° C. for 1 h. Than the [4-[(5-bromopentyl)oxy]-5-(methyloxy)-2-nitrophenyl](2S)-2-[di(ethylsulfanyl)methyl]tetrahydro-1H-1-pyrrolylmethanone 2c (549 mg, 1 mmol). The reaction mixture was stirred at room temperature for 12 h. TLC using ethylacetate as a solvent system monitored the reaction. The potassium phosphate was removed by suction filtration and the solvent was removed under vacuum. The crude product was purified by column chromatography using petroleum ether-ethylacetate (1:1) as eluent to afford pure compound of 7c (651 mg, 75%). ESIMS: m/z 868 ($M^+$)

$^1$H NMR ($CDCl_3$): δ 8.61 (d, J=7.365, 2H), 8.23 (d, J=8.120 Hz, 2H), 7.77 (t, J=7.554, 2H), 7.66 (s, 1H), 6.82 (s, 1H), 4.88 (d, J=3.588 Hz, 1H), 4.76-4.66 (m, 1H), 4.36-4.22 (m, 4H), 4.09 (t, J=6.043, 2H), 3.95 (s, 3H), 3.32 (t, J=7.365, 2H), 3.28-3.21 (m, 1H), 2.88-2.65 (m, 4H), 2.61-2.48 (m, 5H), 2.36-2.21 (m, 2H), 2.20-2.03 (m, 2H), 2.02-1.87 (m, 3H), 1.86-1.71 (m, 3H), 1.70-1.51 (m, 3H), 1.47-1.22 (m, 6H), 1.03-0.82 (m, 3H).

The compound 7c (868 mg, 1 mmol) dissolved in methanol (20 mL) and added $SnCl_2.2H_2O$ (1.125 g, 5 mmol) was refluxed for 5 h or until the TLC indicated that reaction was completed. The methanol was evaporated by vacuum and the aqueous layer was then carefully adjusted to pH 8 with 10% $NaHCO_3$ solution and then extracted with ethyl acetate and chloroform (2×30 ml and 2×30 mL). The combined organic phase was dried over $Na_2SO_4$ and evaporated under vacuum to afford the crude amino diethyl thioacetal 10c (653 mg, 78%), which was used directly in the next step.

A solution of 10c (838 mg, 1 mmol), $HgCl_2$ (613 mg, 2.26 mmol) and $CaCO_3$ (246 mg, 2.46 mmol) in acetonitrile-water (4:1) was stirred slowly at room temperature for overnight or until TLC indicates complete loss of starting material. The reaction mixture was diluted with ethyl acetate (30 ml) filtered through a celite. The clear organic supernatant was extracted with saturated 5% $NaHCO_3$ (20 ml), brine (20 ml) and the combined organic phase is dried ($Na_2SO_4$). The organic layer was evaporated in vacuum and purified by column chromatography (95% $CH_2Cl_2$-MeOH) to give compound 13c (392 mg, 55%). This material was repeatedly evaporated from $CHCl_3$ in vacuum to generate the imine form.

Example 7

To a solution of 1-methylhexahydropyrazine of formula 5 (100 mg, 1 mmol) in dry acetone (10 mL) was added carbon disulfide 10 drops (~2.5 mmol) and anhydrous $K_3PO_4$ (425 mg, 2 mmol). The mixture was stirred <10° C. for 1 h. Than the [4-[(4-bromobutyl)oxy]-5-(methyloxy)-2-nitrophenyl](2S)-2-[di(ethylsulfanyl)methyl]-tetrahydro-1H-1-pyrrolylmethanone 2b (535 mg, 1 mmol). The reaction mixture was stirred at room temperature for 12 h. TLC using ethylacetate as a solvent system monitored the reaction. The potassium phosphate was removed by suction filtration and the solvent was removed under vacuum. The crude product was purified by column chromatography using petroleum ether-ethylacetate (1:1) as eluent to afford pure compound of 8a (504 mg, 80%).

$^1$NMR ($CDCl_3$): δ 7.63 (s, 1H), 6.77 (s, 1H), 4.88-4.79 (d, 1H), 4.77-4.59 (m, 1H), 4.21-4.08 (t, J=5.816 Hz, 2H), 3.95 (s, 3H), 3.44-3.33 (t, J=6.647, 2H), 3.32-3.18 (m, 2H), 2.91-2.63 (m, J=4.985, 4H), 2.33 (s, 3H), 2.16-1.87 (m, 4H), 1.42-1.23 (m, 6H).

The compound 8a (631 mg, 1 mmol) dissolved in methanol (20 mL) and added $SnCl_2.2H_2O$ (1.125 g, 5 mmol) was refluxed for 5 h or until the TLC indicated that reaction was completed. The methanol was evaporated by vacuum and the aqueous layer was then carefully adjusted to pH 8 with 10% $NaHCO_3$ solution and then extracted with ethyl acetate and chloroform (2×30 ml and 2×30 mL). The combined organic phase was dried over $Na_2SO_4$ and evaporated under vacuum to afford the crude amino diethyl thioacetal 11a (468 mg, 78%), which was used directly in the next step.

A solution of 11a (601 mg, 1 mmol), $HgCl_2$ (613 mg, 2.26 mmol) and $CaCO_3$ (246 mg, 2.46 mmol) in acetonitrile-water (4:1) was stirred slowly at room temperature for overnight. The reaction mixture was diluted with ethyl acetate (30 mL) filtered through a celite pad. The clear organic supernatant was extracted with saturated 5% $NaHCO_3$ (20 mL), brine (20 mL) and the combined organic phase was dried ($Na_2SO_4$). The organic layer was evaporated under vacuum and purified by column chromatography using MeOH—$CHCl_3$ (4%) to give compound 14a (276 mg, 58%). This material was repeatedly evaporated from $CHCl_3$ in vacuum to generate the imine form. ESIMS: m/z 477 ($M^+$)

$^1$H NMR ($CDCl_3$): δ 7.61 (s, J=4.688, 1H), 7.45 (s, 1H), 6.73 (s, 1H), 4.07-3.80 (m, 4H), 3.79 (s, 3H), 3.74-3.61 (m, 2H), 3.3 (t, J=7.031, 4H), 2.44 (t, J=5.469, 2H), 2.27 (s, 3H), 2.05-1.77 (m, 4H), 1.54-1.51 (m, 1H), 1.36 (d, J=5.469, 1H), 1.25-1.06 (m, 3H), 0.92-0.74 (m, 2H).

Example 8

To a solution of 1-methylhexahydropyrazine of formula 5 (100 mg, 1 mmol) in dry acetone (10 mL) was added carbon disulfide 10 drops (~2.5 mmol) and anhydrous $K_3PO_4$ (425 mg, 2 mmol). The mixture was stirred <10° C. for 1 h. Than the [4-[(5-bromopentyl)oxy]-5-(methyloxy)-2-nitrophenyl](2S)-2-[di(ethylsulfanyl)methyl]tetrahydro-1H-1-pyrrolylmethanone 2c (549 mg, 1 mmol). The reaction mixture was stirred at room temperature for 12 h. TLC using ethylacetate as a solvent system monitored the reaction. The potassium phosphate was removed by suction filtration and the solvent was removed under vacuum. The crude product was purified by column chromatography using petroleum ether-ethylacetate (1:1) as eluent to afford pure compound of 8b (516 mg, 80%).

$^1$NMR ($CDCl_3$): δ 7.67 (s, 1H), 6.83 (s, 1H), 4.91-4.86 (d, 1H), 4.78-4.65 (m, 1H), 4.10 (t, J=7.036 Hz, 2H), 3.96 (s, 3H), 3.36 (t, 2H, J=7.036), 3.30-3.21 (m, 2H), 2.88-2.75 (m, 4H), 2.52 (t, J=5.472, 4H) 2.35 (s, 3H), 2.30-2.17 (m, 2H), 2.12 (t, 2H, J=7.818), 2.07-2.00 (m, 2H), 1.94 (t, J=7.818, 2H), 1.88-1.75 (m, 2H), 1.67 (t, J=3.909, 2H), 1.65-1.57 (m, 2H), 1.41-1.21 (m, 6H)

The compound 8b (645 mg, 1 mmol) dissolved in methanol (20 mL) and added $SnCl_2.2H_2O$ (1.125 g, 5 mmol) was refluxed for 5 h or until the TLC indicated that reaction was completed. The methanol was evaporated by vacuum and the aqueous layer was then carefully adjusted to pH 8 with 10% $NaHCO_3$ solution and then extracted with ethyl acetate and chloroform (2×30 ml and 2×30 mL). The combined organic phase was dried over $Na_2SO_4$ and evaporated under vacuum to afford the crude amino diethyl thioacetal 11b (479 mg, 78%), which was used directly in the next step.

A solution of 11b (615 mg, 1 mmol), $HgCl_2$ (613 mg, 2.26 mmol) and $CaCO_3$ (246 mg, 2.46 mmol) in acetonitrile-water (4:1) was stirred slowly at room temperature for overnight. The reaction mixture was diluted with ethyl acetate (30 mL) filtered through a celite pad. The clear organic supernatant was extracted with saturated 5% $NaHCO_3$ (20 mL), brine (20 mL) and the combined organic phase was dried ($Na_2SO_4$). The organic layer was evaporated under vacuum and purified by column chromatography using MeOH—$CHCl_3$ (4%) to give compound 14b (284 mg, 58%). This material was repeatedly evaporated from $CHCl_3$ in vacuum to generate the imine form. ESIMS: m/z 491 ($M^+$)

$^1H$ NMR ($CDCl_3$): δ 7.62 (s, J=3.906, 1H), 7.47 (s, 1H), 6.75 (s, 1H), 4.10-3.94 (m, 4H), 3.89 (s, 3H), 3.83-3.64 (in, 1H), 3.62-3.48 (m, 2H), 3.47-3.39 (m, 2H), 3.29 (t, J=7.031, 2H), 2.45 (t, J=5.469, 4H) 2.29 (s, 3H), 2.35-2.21 (m, 2H), 2.09-1.94 (m, 2H), 1.93-1.80 (m, 2H), 1.75 (t, J=7.813, 2H), 1.65-1.50 (m, 2H).

Biological Activity:

DNA Binding Affinity of New pyrrolo[2,1-c][1,4]benzodiazepine Derivatives with dithiocarbamate Side Chains of General Formula 12b-d, 13b-d, 14c-d Compounds have been subjected to thermal denaturation studies with duplex-form calf thymus DNA (CT-DNA) using an modification of a reported procedure (Newman, M. S. *Carcinog-compr. Surv.* 1976, 1, 203; (b) Hecht, S. S.; Loy, M.; Hoffman, *Carcinog-compr. Surv.* 1976, 1, 325). Working solutions in aqueous buffer (10 mM $NaH_2PO_4/Na_2HPO_4$, 1 mM $Na_2EDTA$, pH 7.00+0.01) containing CT-DNA (100 μm in phosphate) and the PBD (20 μm) have been prepared by addition of concentrated PBD solutions in DMSO to obtain a fixed [PBD]/[DNA] molar ratio of 1:5. The DNA–PBD solutions have been incubated at 37° C. for 0 and 18 h prior to analysis. Samples have been monitored at 260 nm using a Beckman DU-800 spectrophotometer fitted with high performance temperature controller, and heated at 1° C. $min^{-1}$

TABLE 1

Thermal denaturation data for pyrrolo[2,1-c][1,4]benzodiazepine derivatives with dithiocarbamate side chains with calf thymus (CT) DNA

| PBD hybrids | [PBD]:[DNA] molar ratio[b] | ($\Delta T_m$° C.)[a] after incubation at 37° C. for 0 h | 18 h |
|---|---|---|---|
| 12b | 1:5 | 2.0 | 4.0 |
| 12c | 1:5 | 2.0 | 2.1 |
| 12d | 1:5 | 2.0 | 2.1 |
| 13b | 1:5 | 3.1 | 3.3 |
| 13c | 1:5 | 5.0 | 5.0 |
| 13d | 1:5 | 4.0 | 4.6 |
| 14c | 1:5 | 2.1 | 2.2 |
| 14d | 1:5 | 6.0 | 10.9 |
| DC-81 | 1:5 | 0.3 | 0.7 |

[a]For CT-DNA alone at pH 7.00 ± 0.01, $T_m$ = 69.1° C. ± 0.01 (mean value from 10 separate determinations), all $\Delta T_m$ values are ±0.1-0.2° C.

[b]For a 1:5 molar ratio of [PBD]/[DNA], where CT-DNA concentration = 100 μM and ligand concentration = 20 μM in aqueous sodium phosphate buffer [10 mM sodium phosphate + 1 mM EDTA, pH 7.00 ± 0.01].

in the 40-110° C. range. DNA helix□coil transition temperatures ($T_m$) have been obtained from the maxima in the $d(A_{260})/dT$ derivative plots. Drug-induced alterations in DNA melting behavior are given by: $\Delta T_m = T_m(\text{DNA+PBD}) - T_m$ (DNA alone), where the $T_m$ value for the PBD-free CT-DNA is 69.1±0.01. The fixed [PBD]/[DNA] ratio used has not resulted in binding saturation of the host DNA duplex for any compound examined.

The DNA binding activity for these new pyrrolo[2,1-c][1,4]benzodiazepine derivatives with dithiocarbamate side chains of general formula 12b-d has been examined by thermal denaturation studies using calf thymus (CT) DNA. Melting studies show that these compounds stabilize the thermal helix □ coil or melting stabilization ($\Delta T_m$) for the CT-DNA duplex at pH 7.0, incubated at 37° C., where PBD/DNA molar ratio is 1:5. The data for the compounds 12b-d, is included in Table 1 for comparison.

Anticancer Activity:

In vitro anticancer activity studies for the compounds 12b-c were carried out at the National Cancer Institute (USA). The compounds 12b-c were evaluated for in vitro anticancer activity against sixty human tumour cells derived from nine cancer types (leukemia, non-small-cell lung, colon, CNS, melanoma, ovarian, prostate, and breast cancer) as per NCI protocol. For each compound, dose response curves for each cell line were measured at a minimum of five concentrations at 10 fold dilutions. A protocol of 48 h continuous drug exposure was used and a sulforhodamine B (SRB) protein assay was used to estimate cell viability or growth. The concentration causing 50% cell growth inhibition (G150), total cell growth inhibition (TGI 0% growth) and 50% cell death (LC50, −50% growth) compared with the control was calculated.

Compound 12b has been evaluated for in vitro cytotoxicity in sixty cell lines from nine human cancer types of leukemia (MOLT-4, SR), lung (Hop-62, NCI-H522), colon (HCT-116, SW-620), CNS (SF268), melanoma (LOX IMVI, MALME-3M), ovarian (IGROV1, OVCAR-3, OVCAR-8), renal (CAKI-1, RXF 393), prostate (DU-145), breast (MCF-7, MDA-MB-468) origin.

Compound 12c has been evaluated for in vitro cytotoxicity in sixty cell lines from nine human cancer types of leukemia (HL-60 (TB), SR), lung (Hop-62, HOP-92, NCI-H522), colon (HCT-116, HT-29, SW-620), CNS (U251), melanoma (LOX IMVI, SK-MEL-2), ovarian (IGROV1), renal (RXF 393, UO-31), prostate (PC3), breast (MCF-7, MDA-MB-468) origin.

The results are expressed as percent of cell growth determined relative to that of untreated control cells (Table 3). The representative compound 12b has shown significant cytotoxicity against some cancer cell lines.

TABLE 2

$Log_{10}$ GI50 (concentration in mol/L) and $Log_{10}$ LC50 (concentration in mol/L causing 50% lethality) values for the representative compounds 12b and 12c

| | $Log_{10}$ GI50 | | $Log_{10}$ LC50 | |
|---|---|---|---|---|
| Cancer panel | 12b | 12c | 12b | 12c |
| Leukemia | −6.63 | −6.26 | −4.26 | −4.00 |
| Non-small-cell-lung | −6.07 | −5.97 | −4.96 | −4.41 |
| Colon | −6.02 | −5.93 | −5.07 | −4.14 |
| CNS | −6.12 | −5.84 | −5.35 | −5.12 |
| Melanoma | −5.94 | −5.90 | −5.26 | −5.13 |
| Ovarian | −6.03 | −5.82 | −4.73 | −4.26 |
| Renal | −6.20 | −6.05 | −5.39 | −4.82 |
| Prostate | −6.51 | −5.99 | −5.62 | −5.14 |
| Breast | −6.13 | −6.02 | −4.43 | −4.18 |

each cancer type represents the average of six to eight different cancer cell lines.

The compound 12b exhibits a wide spectrum of activity against sixty cell lines in nine cell panels, with $GI_{50}$ value of <2.69 μm. In the non-small cell lung cancer panel, the growth of HOP-62, NCI-H522 cell lines were affected by compound 12b with $GI_{50}$ values as 0.21 and 0.17 ρm respectively. The $GI_{50}$ values of compound 12b against colon cancer HCT-116 and SW-620 cell lines are 0.38 and 0.51 μm respectively. The $GI_{50}$ values for compound 12b against leukemia MOLT-4 and SR cell lines are 0.22, 0.18 μm respectively. The $GI_{50}$ values for compound 12b against CNS SF268 cell line is 0.28 μm. The $GI_{50}$ values for compound 12b against melanoma LOX IMVI and MALME-3M cell lines are 0.60, and 0.93 μm respectively. The $GI_{50}$ values for compound 12b against ovarian IGROV1, OVCAR-3 and OVCAR-8 cell lines are 0.30, 0.28 and 0.99 μm. The $GI_{50}$ values for compound 12b against renal CAKI-1 and RXF 393 cell lines are 0.30 and 0.19 μM. The $GI_{50}$ value for compound 12b against prostate DU-145 cell line is 0.26 μm. The $GI_{50}$ values for compound 12b against breast MCF-7 and MDA-MEI-468 cell lines are 0.33 and 0.28 μm respectively.

Compounds 12b and 12c exhibit activity against sixty cell lines in nine cancer cell panels with $GI_{50}$ values of <2.69 and <3.29 □M respectively. Compare 12b and 12c, the compound 12b showing higher activity than 12c, In vitro cytotoxicity of compounds 12b and 12c in selected cancer cell lines have been illustrated in Table 3. The average $GI_{50}$ values for each cancer panel of compounds 12b and 12c have been illustrated in Table 2

TABLE 3

In vitro cytotoxicity of compounds 12b and 12c in selected cancer cell lines

| Cancer panel/cell line | $GI_{50}$ (μM) 12b | 12c |
|---|---|---|
| Leukemia | | |
| CCRF-CEM | 0.23 | 0.53 |
| HL-60(TB) | 0.25 | 0.32 |
| K-562 | 0.26 | 3.29 |
| MOLT-4 | 0.22 | 0.35 |
| RPMI-8226 | 0.22 | 0.49 |
| SR | 0.18 | 0.25 |
| Non-smallcell lung | | |
| A549/ATCC | 1.22 | 1.61 |
| EKVX | 2.29 | 1.88 |
| HOP-62 | 0.12 | 0.71 |
| HOP-92 | 1.07 | 1.07 |
| NCI-H226 | 1.51 | 1.26 |
| NCI-H23 | 1.40 | 1.68 |
| NCI-H322M | 1.87 | 1.40 |
| NCI-H460 | 0.77 | 1.25 |
| NCI-H522 | 0.17 | 0.19 |
| Colon | | |
| COLO 205 | 1.30 | 1.40 |
| HCC-2998 | 1.64 | 1.57 |
| HCT-116 | 0.38 | 0.54 |
| HCT-15 | 1.81 | 1.41 |
| HT29 | 0.87 | 1.13 |
| KM12 | 1.07 | 1.39 |
| SW-620 | 0.51 | 1.12 |
| CNS | | |
| SF-268 | 0.28 | 1.23 |
| SF-539 | 1.44 | 1.69 |
| SNB-19 | 1.23 | 1.67 |
| SNB-75 | 1.26 | 1.64 |
| U251 | 0.39 | 1.11 |
| Melanoma | | |
| LOX IMVI | 0.60 | 0.69 |
| MALME-3M | 0.93 | 1.36 |
| M14 | 1.17 | 1.25 |
| SK-MEL-2 | 1.16 | 1.04 |
| Ovarian | | |
| IGROV1 | 0.30 | 0.42 |
| OVCAR-3 | 0.28 | 1.20 |
| OVCAR-4 | 2.11 | 1.82 |
| OVCAR-5 | 1.35 | 2.47 |
| OVCAR-8 | 0.99 | 1.59 |
| SK-OV-3 | 2.69 | 2.96 |
| Renal | | |
| 786-0 | 1.06 | 1.28 |
| A498 | 0.91 | 1.19 |
| ACHN | 0.94 | 1.16 |

TABLE 3-continued

In vitro cytotoxicity of compounds 12b and 12c in selected cancer cell lines

| Cancer panel/cell line | $GI_{50}$ (μM) 12b | 12c |
|---|---|---|
| CAKI-1 | 0.30 | 0.59 |
| RXF 393 | 0.19 | 0.41 |
| SN12C | 0.64 | 1.16 |
| TK-10 | 0.65 | 1.26 |
| UO-31 | 1.10 | 0.59 |
| Breast | | |
| MCF7 | 0.33 | 0.43 |
| MDA-MB- | 1.41 | 1.53 |
| HS 578T | 0.56 | 0.72 |
| MDA-MB-435 | 0.55 | 1.04 |
| BT-549 | 0.92 | 1.42 |
| T-47D | 0.57 | 0.57 |
| MDA-MB-468 | 0.28 | 0.49 |
| Prostate | | |
| PC-3 | 0.34 | 0.69 |
| DU-145 | 0.26 | 1.47 |
| Melanoma | | |
| SK-MEL-28 | 1.52 | 1.75 |
| SK-MEL-5 | 1.18 | 1.11 |
| UACC-257 | 2.00 | 1.97 |
| UACC-62 | 1.06 | 1.32 |

The mean graph mid point values of $\log_{10}$ TGI and $\log_{10}$ $LC_{50}$ as well as $\log_{10}$ $GI_{50}$ for 12b and 12c are listed in Table-5. As demonstrated by mean graph pattern, compounds 12b and 12c exhibit an interesting profile of activity and selectivity for various cell lines. The mean graph mid points of $\log_{10}$ TGI and $\log_{10}$ $LC_{50}$ have shown similar pattern to the $\log_{10}$ $GI_{50}$ mean graph mid points.

TABLE 4

$Log_{10}$GI50 $log_{10}$TGI and $log_{10}$LC50 mean graphs midpoints (MG_MID) of in vitro cytotoxicity data for the representative compounds against human tumour cell lines

| Compound | $Log_{10}$GI50 | $Log_{10}$TGI | $Log_{10}$LC50 |
|---|---|---|---|
| 12b | −6.15 | −5.67 | −4.96 |
| 12c | −5.98 | −5.28 | −4.48 |

Further the compounds 12c, 14c-d were examined for preliminary in vitro cytotoxicity on six cell lines.

TABLE 5

Preliminary in vitro cytotoxicity data for the compounds 12c and 14c-d at concentration (mg/ml) 1 × $10^{-5}$ M, Adriamycin at concentration (mg/ml) 1 × $10^{-6}$ M

| Compound | Lung A-549 | Colon HCT-15 | Neuro-blastoma IMR-32 | Ovary OVCAR-5 | Liver HEP-2 | Colon 502713 |
|---|---|---|---|---|---|---|
| 12c | 31 | 75 | 88 | 24 | 69 | 75 |
| 14c | 50 | 82 | 86 | 36 | 66 | 75 |
| 14d | 31 | 50 | 95 | 22 | 66 | 78 |
| Adria-mycin | 61 | 58 | 80 | 30 | 31 | — |

Significance of the Work Carried Out

The new pyrrolo[2,1-c][1,4]benzodiazepine derivatives with dithiocarbamate side chains that have been synthesized exhibited significant DNA-binding ability and showed cytotoxic activity against sixty human tumour cell lines.

ADVANTAGES OF THE INVENTION

1. The present invention provides a new pyrrolo[2,1-c][1,4]benzodiazepine derivatives with dithiocarbamate side chains useful as antitumour agents.
2. It also provides a process for the preparation of novel pyrrolo[2,1-c][1,4]benzodiazepine hybrids.

We claim:

1. A compound of formula A

Formula A

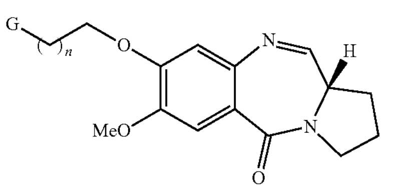

n = 1-9 wherein G =

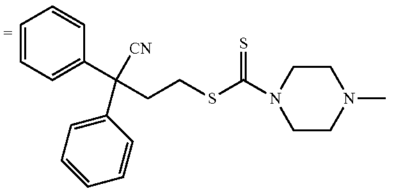

or

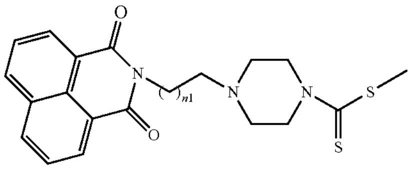

or where $n_1$ = 2.

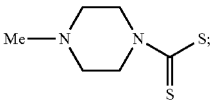

2. A process for the preparation of a compound of Formula A according to claim 1 comprising the steps of:

a) reacting (2S)-2[di(ethylsulfanyl)methyl]tetrahydro-1H-1-pyrrolyl[4-hydroxy-5-(methyloxy)-2-nitrophenyl] methanone of formula 1 with dibromoalkanes in presence of acetone/$K_2CO_3$ at reflux temperature for a period of 48 h, isolating [4-[(n-bromoalkyl)oxy]-5-(methyloxy)-2-nitrophenyl](2S)-2-[di(ethylsulfanyl)methyl]tetrahydro-1H-1-pyrrolylmethanone 2a-i, reacting these compounds with 3-cyano-3,3-diphenylpropyl-hexahydro-1-pyrazinecarbodi-thioate 3,2-(3-hexahydro-1-pyrazinylpropyl)-2,3-dihydro-1H-benzo[de]isoquinoline-1,3-dione 4, and 1-methylhexahydropyrazine of formula 5, isolating 3-cyano-3,3-diphenylpropyl 4-(n-[4-((2S)-2-[di(ethylsulfanyl)methyl]tetrahydro-1H-1-pyrrolyl-carbonyl)-2-(methyloxy)-5-nitrophenyl]oxyalkyl)hexahydro-1-pyrazinecarbodithioate of formula 6a-i, n-[4-((2S)-2-[di(ethylsulfanyl)methyl]-tetrahydro-1H-1-pyrrolylcarbonyl)-2-(methyloxy)-5-nitrophenyl]oxyalkyl 4-[3-(1,3-dioxo-2,3-dihydro-1H-ben-zo[de]isoquinolin-2-yl)propyl]hexahydro-1-pyrazinecarbodithioate of formula 7a-i and 3-[4-((2S)-2-[di(ethylsulfanyl)methyl]tetrahydro-1H-1-pyrrolylcarbonyl)-2-(methyloxy)-5-nitrophenyl]oxyalkyl 4-methylhexahydro-1-pyrazinecarbodithioate of formula 8a-i respectively, b) reducing the above nitro compounds of formula 6a-i, 7a-i and 8a-i with $SnCl_2.2H_2O$ in presence of organic solvent selected from methanol and ethanol up to a reflux temperature, isolating the 3-cyano-3,3-diphenylpropyl 4-(n-[5-amino-4-((2S)-2-[di(ethylsulfanyl)methyl]tetrahydro-1H-1-pyrrolylcarbonyl)-2-(methyloxy)phenyl]oxyalkyl)hexahydro-1-pyrazinecarbodithioate of formula 9a-i, n-[5-amino-4-((2S)-2-[di(ethylsulfanyl)methyl]tetrahydro-1H-1-pyrrolylcarbonyl)-2-(methyloxy)phenyl]oxyalkyl 4-[3-(1,3-dioxo-2,3-dihydro-1H-benzo[de]iso-quinolin-2-yl)propyl]hexahydro-1-pyrazinecarbodithioate of formula 10a-i, and n-[5-amino-4-((2S)-2-[di(ethylsulfanyl)methyl]tetrahydro-1H-1-pyrrolylcarbonyl)-2-(methyloxy)phenyl]oxyalkyl 4-methylhexahydro-1-pyrazinecarbodithioate of formula 11a-i, respectively, c) reacting the above amino compounds of formula 9a-i, 10a-i and 11a-i with known deprotecting agents in a conventional manner to obtain pyrrolo[2,1-c][1,4]benzodiazepine hybrids of formula 12a-i, 13a-i and 14a-i.

3. The compound of claim 1, having the formula 12a-i

Formula 12 a-i

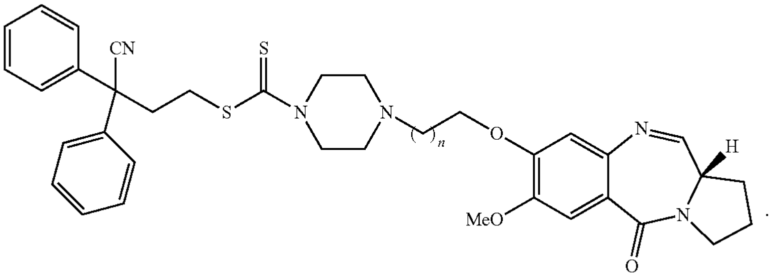

wherein n = 1-9

4. The compound of claim 1, having the formula 13a-i:

Formula 13a-i

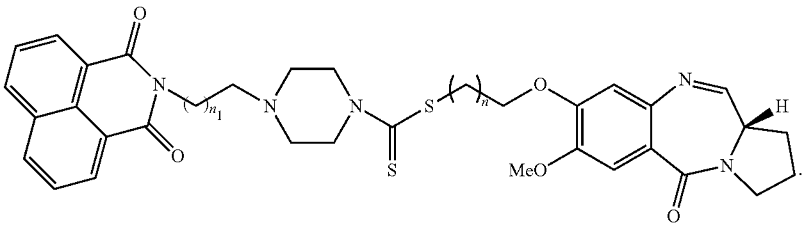

where $n_1$ is 2, and n is 1-9

5. The compound of claim 1, having the formula 14a-i:

Formula 14a-i

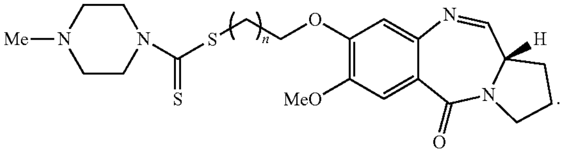

where n is 1-9

6. A method of treating cancer comprising administering a compound of Formula A according to claim 1 to a subject in need thereof, wherein the cancer is selected from the group consisting of leukemia, non-small-cell lung cancer, colon cancer, CNS cancer, melanoma, ovarian cancer, prostate cancer, and breast cancer.

* * * * *